United States Patent
Repperger et al.

(10) Patent No.: US 6,736,015 B1
(45) Date of Patent: May 18, 2004

(54) ROBUST, WIRELESS MICROELECTRO MECHANICAL SYSTEM (MEMS) SHEAR FORCE SENSOR

(75) Inventors: Daniel W. Repperger, Dayton, OH (US); David B. Reynolds, Beavercreek, OH (US); James Berlin, Huber Heights, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 10/286,713

(22) Filed: Nov. 4, 2002

(51) Int. Cl.[7] .................................................. G01N 3/24
(52) U.S. Cl. ...................... 73/841; 73/815; 73/862.325; 73/862.043
(58) Field of Search ............................ 73/841–846, 788, 73/808, 815, 862.325, 862.043, 862.639

(56) References Cited

U.S. PATENT DOCUMENTS

| | | | |
|---|---|---|---|
| 5,341,687 A | * | 8/1994 | Stan ........................ 73/862.046 |
| 5,459,382 A | * | 10/1995 | Jacobus et al. ......... 318/568.11 |
| 5,528,452 A | | 6/1996 | Ko ............................ 361/283.4 |
| 5,553,500 A | * | 9/1996 | Grahn et al. .................... 73/628 |
| 5,571,973 A | * | 11/1996 | Taylot ..................... 73/862.046 |
| 5,604,314 A | | 2/1997 | Grahn .......................... 73/628 |
| 5,871,248 A | | 2/1999 | Okogbaa et al. ........... 294/86.4 |
| 2002/0092364 A1 | * | 7/2002 | Adderton et al. ......... 73/862.41 |

* cited by examiner

Primary Examiner—Edward Lefkowitz
Assistant Examiner—Alandra Ellington
(74) Attorney, Agent, or Firm—Gina S. Tollefson; Gerald B. Hollins; Thomas L. Kundert

(57) ABSTRACT

Micro electromechanical components in a novel configuration to allow wireless normal direction pressure transducers to be used for oblique or shear forces. The invention includes a novel cantilever beam configuration and algorithm, the readings of the MEMS sensors are averaged to reduce the experimental variability, to estimate the shear stress that may occur between a human and external equipment or possibly between materials. The shear force component is calculated via the formula:

$$\text{Shear Force} = V_t = \sqrt{\overline{V}^2_{3+4+\ldots+n_1} - \overline{V}^2_{1+2+\ldots+n_2}}.$$

18 Claims, 5 Drawing Sheets

ROBUST, WIRELESS MICROELECTRO MECHANICAL SYSTEM (MEMS) SHEAR FORCE SENSOR

RIGHTS OF THE GOVERNMENT

The invention described herein may be manufactured and used by or for the Government of the United States for all governmental purposes without the payment of any royalty.

BACKGROUND OF THE INVENTION

Sensing shear force has received considerable interest in recent times for a number of practical reasons. Piezoresistive materials have applicability since the resistive properties of a material may change due to shear force. Optical means of sensing shear force are possible as light and the lens through which it passes is changed due to shear stress. Another way shear force sensing is commonly accomplished is by using ultrasonic transducers, and a graphical rendering of such stresses is possible via a computer.

The motivation for knowing shear forces has much utility. In robotics, it allows the determination of the existing friction in picking up objects. It enables the user to ascertain the required force to lift objects of various densities. If an object contains a fabric, this information can be conveyed to a remote operator through the shear force sensing mechanism. For all types of grasping and manipulation, measurement of the forces and pressure points is important when humans contact clothing, shoes, boots, sporting equipment, industrial implements (hand tools, etc), and for determination of balance and gait analysis for athletic training. The applications also include medical treatment and rehabilitation, for accelerometers and numerous other purposes where an additional dimension of force needs to be properly sensed and fed back to the user.

To define more precisely how the term "shear force" is to be used, herein, FIG. 1 illustrates a force vector V, shown at 103, acting on a mass, 100, at an oblique angle θ, 102. The vector V 103 can be decomposed into two vectors: at 104 $V_n$ is a normal vector which acts on the mass in a direction perpendicular to the ground, and at 101 $V_t$, is the component of the force vector V which is transverse to the ground (shear force) and is perpendicular to the normal force. V 103 is the vector sum of $V_n$, 104 and $V_t$ 101 since they act at right angles. The magnitude of V 103 can be expressed, using the hypotenuse rule for right triangles, as:

$$|V|^2 = |V_n|^2 + |V_t|^2 \quad \text{Eq. 1}$$

By using equation (1), the shear force term $V_t$ can be computed.

SUMMARY OF THE INVENTION

The invention uses micro electromechanical components in a novel configuration to allow wireless normal direction pressure transducers to be used for measurement of oblique or shear forces. The invention includes a novel cantilever beam configuration and algorithm, the readings of the MEMS sensors are averaged to reduce the experimental variability, to estimate the shear stress that may occur between a human and external equipment or possibly between materials. The shear force component is calculated via the formula:

$$\text{Shear Force} = V_t = \sqrt{\overline{V^2}_{3+4+\ldots+n_1} - \overline{V^2}_{1+2+\ldots+n_2}}$$

It is therefore an object of the invention is to provide a mechanical-electrical shear force sensing apparatus.

Another object of the invention is to provide a wireless shear force sensing apparatus.

Another object of the invention to provide a mechanical-electrical shear force sensing apparatus with reduced variability.

Another object of the invention is to provide a mechanical-electrical shear force sensing apparatus operable through nonmetallic materials.

These along with other objects of the invention described in the description, claims and drawings are achieved by a sensing apparatus responsive to shear forces comprising:

a first plurality of mechanical-electrical sensing components integral with a first rectangular structure and sensing normal forces;

a second plurality of mechanical-electrical sensing components integral with a second rectangular structure adjacent and in a cantilever beam configuration to said first rectangular structure and sensing both normal and transverse forces;

microelectronic processing means for reading force data obtained by said mechanical-electrical sensing components, temperature, and individual mechanical-electrical sensing component identifying data; and an operator interfacing external antenna transmitting power and an instructional signal to said mechanical-electrical sensing components and thereafter receiving said force, temperature and sensing component identifying data from said microelectronic processing means to determine shear force according to the relationship $$\text{Shear Force} = V_t = \sqrt{\overline{V^2}_{3+4+\ldots+n_1} - \overline{V^2}_{1+2+\ldots+n_2}}$$

DETAILED DESCRIPTION

Figure 1:
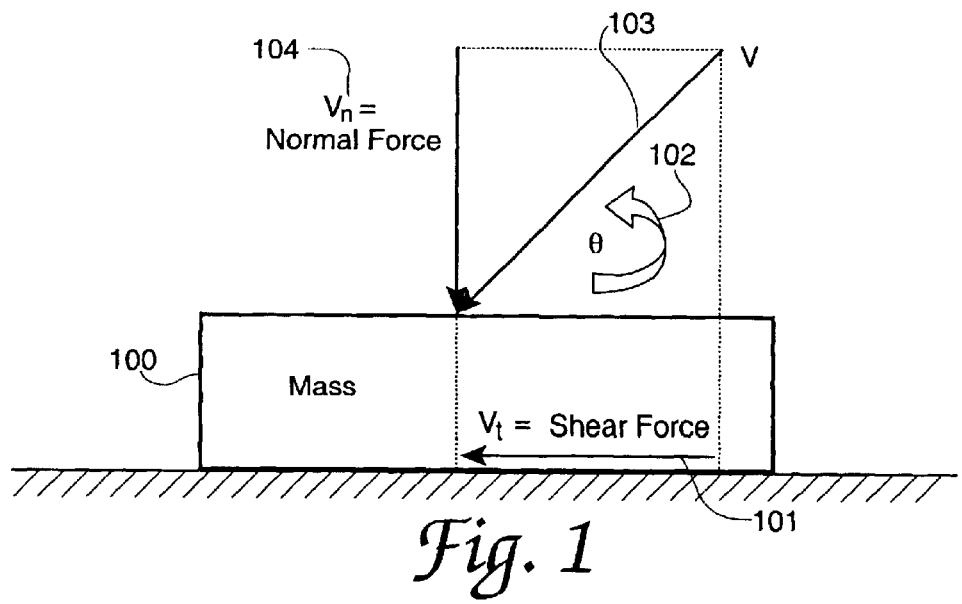
FIG. 1 illustrates a force vector V acting on a mass at an oblique angle Θ.
Figure 2:
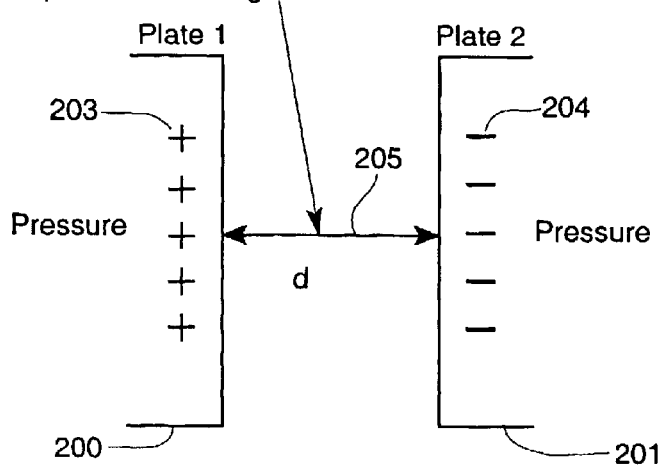
FIG. 2 illustrates how MEMS senses pressure or force.

To understand the arrangement of the invention, measuring normal forces using a MEMs system must first be considered. For measuring normal forces, one way a MEMS force sensor can be constructed is by using the concept of a diaphragm. In FIG. 2, a capacitor is constructed whose inter-electrode distance d, shown at 205, changes as a function of the pressure difference between plate 1 and plate 2, shown at 200 and 201, respectively. If a fixed voltage is applied to the two plates, the charge that builds up is proportional to capacitance. That is:

$$Q + VC \quad \text{Eq. 2}$$

Where V is the voltage applied, C is the effective capacitance and Q is the accumulated charge across the plates. For a capacitor, its capacitance C is a function of the physical inter-electrode distance d, i.e.

$$C \in \mathcal{E} A/d \qquad \text{Eq. 3}$$

where $\in$ is the dielectric constant of the medium between the two plates, A is the effective area between the two plates and d, 205, is their inter-electrode distance. Thus C is strongly sensitive to d, 205, and as the plates, 200 and 201, move toward each other, this capacitance changes significantly. As a consequence of the effect, as d, 205, changes, the charge built up in Eq. 2 rapidly adjusts and an electrical measure of the force or pressure difference between the plates (which moves the plates in a proportional manner) is obtained.

Figure 3:
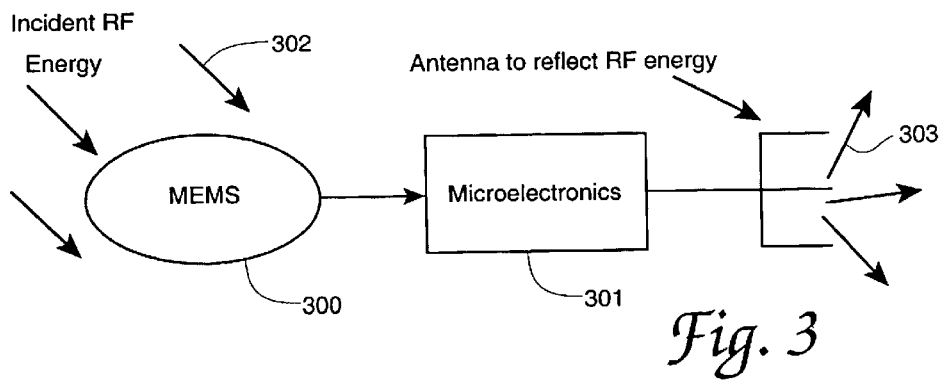
FIG. 3 illustrates communication with the MEMS system.

After the force information is obtained, it is necessary to communicate with the MEMS system to get the information back to the user. FIG. 3 illustrates one possible communication arrangement to sense forces using the MEMs system. All the elements of FIG. 2 are inserted inside the oval labeled "MEMS" and shown at 300 in FIG. 3 and constitute the entire sensing mechanism of the pressure or force. In FIG. 3, it is seen that the overall system is passive, i.e. it does not have any internal power source. To get energy into such a system, radio frequency energy, illustrated at 302, is sent via an external antenna through the airwaves and impinges on the MEMS oval at 300. This incident radio frequency energy not only helps produce a charge difference between the capacitive plates, shown at 201 and 202 in FIG.2, but also powers the microelectronics 301. The microelectronics box 301 reads the pressure, determines the temperature and sends a reflected signal, illustrated at 303, to an antenna on the MEMS chip. This local antenna then broadcasts the following three items of information: pressure reading, temperature, and identification number of the particular MEMS device. The relative size of these elements can be extremely small, about the size of a U.S. nickel coin. What is limiting about the prior technology is that it only measures forces in a normal direction.

Figure 8:
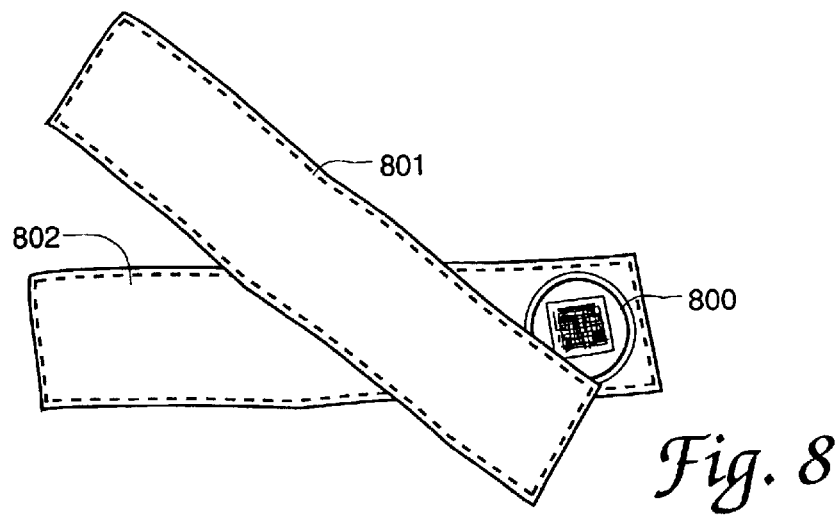
FIG. 8 shows a "force dipstick" arrangement of the invention.

In order to measure forces that may not be perfectly normal, a "Force Dipstick" concept was created. FIG. 8 is a diagram illustrating this concept. Here the MEMS sensor 800 is tightly jammed between two sticks, shown at 801 and 802, made of a rigid material. As this assemblage is inserted into a region of high force or pressure, the two rigid sticks 801 and 802 tend to transfer the force sensed (even at an oblique angle) to a normal component that would be sensed by the MEMS device.

Figure 9:
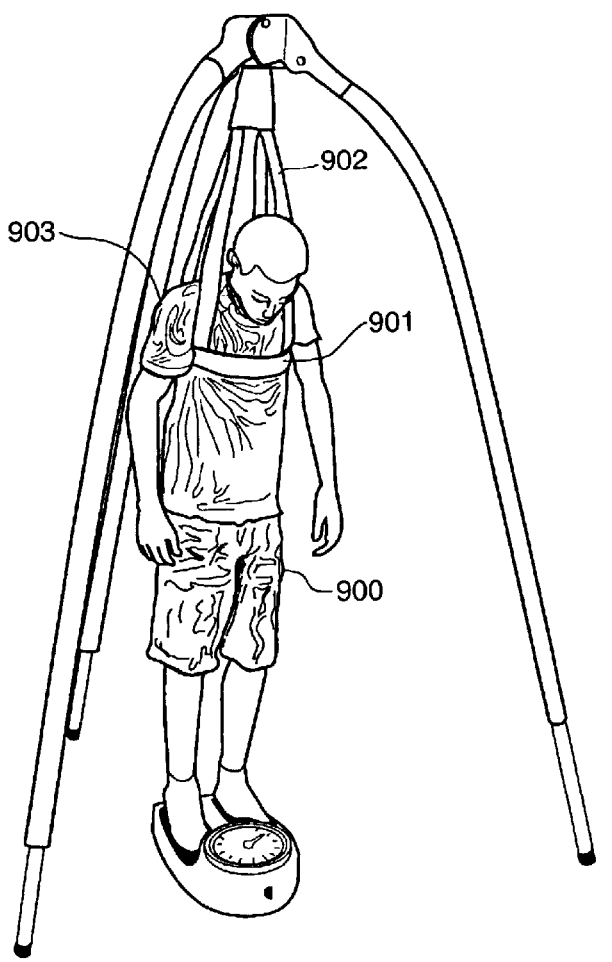
FIG. 9 shows an arrangement of the invention for measuring strap pressure with a child.

FIG. 9 shows an arrangement of the invention for measuring strap pressure with a child. FIG. 9 shows an application in which a child 900 is being partially supported by a strap system 902 and the pressure at the child's back 903 is being sensed with the external antenna. It is also possible for the external antenna to sense pressure at the child's chest 901 with the external antenna. The force "hot spots" occur, in this application, between the strap system and the child's chest. It is desired to measure this force or pressure to assess the level of stress associated with a human using such a strap system. For such an arrangement, the "force dipstick" of FIG. 8 would be inserted between the child at 901 and the strap and the MEMS can measure this pressure through a variety of nonmetallic materials, including human flesh.

Figure 4:
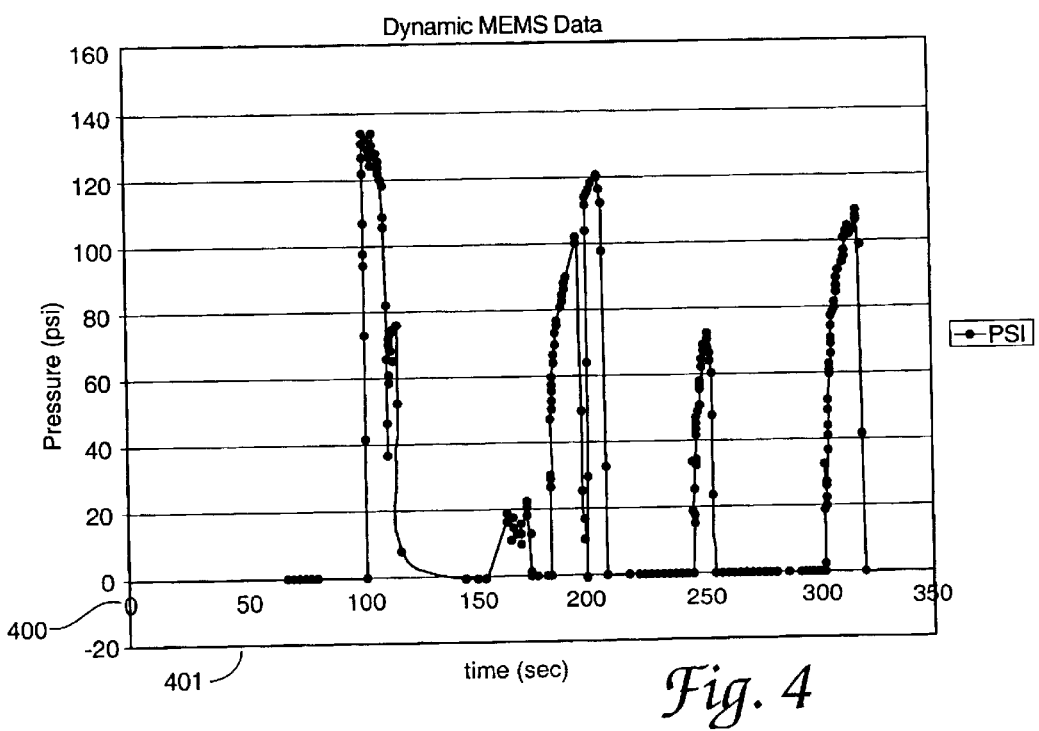
FIG. 4 illustrates dynamic data taken with MEMS.

Dynamic data can also be obtained from the MEMS system described so far. If the child (or adult) were to jump upward in the strap support system in FIG. 9, dynamic data of the force produced are of great interest to assess the risk of using a strap system in a dynamic or temporal sense. In FIG. 4, dynamic data are displayed of an adult jumping in the strap system with the sensors inserted using "force dipsticks" to record the forces or pressures, illustrated at the y-axis 400 versus time at the x-axis 401. The data can be sampled at a rate of about 10 Hz (10 times a second) and the MEMS system has high bandwidth and responsive characteristics. Again, the difficulty so far is that only normal forces can be sensed.

It should be emphasized that the MEMS device so far discussed can easily be inserted inside non-metallic rigid materials. For example, the MEMS device can be inserted inside a transparent composite material. The radio frequency energy can be sent and received through the composite material. Thus, it is possible to read through a material, much like a "Force X-Ray", and the system thus described can read the internal stresses existing between the materials since it is both wireless and requires no internal power source.

Figure 5:
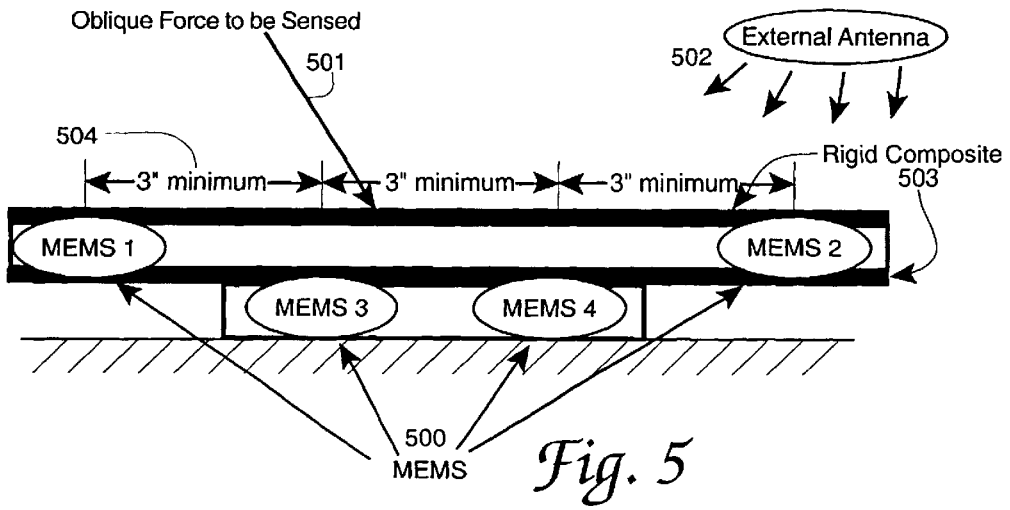
FIG. 5 shows an arrangement of the invention to measure shear forces.

FIG. 5 shows a possible arrangement of the invention for measuring shear force. The arrangement and method of the invention for obtaining the shear stress component $V_t$ follows from the following facts that are relevant about the diagram:

(1) All 4 MEMS devices, shown at 500 in FIG. 5, are initially calibrated with normal forces before testing can commence.

(2) MEMS1 and MEMS2 lie in cantilever beam configuration and they do not experience any transverse stress. They only experience normal stress (the $V_n$ component illustrated at 603 in FIG. 6).

(3) The readings of the MEMS1 and MEMS2 sensors are averaged to reduce the experimental variability in determining the normal component $V_n$.

(4) MEMS3 and MEMS4, however, read the entire force vector V. They experience both normal and transverse stress.

(5) The readings of the MEMS3 and MEMS4 sensors are averaged to reduce the experimental variability in determining the total vector V.

(6) The shear force component is calculated via the formula:

$$\text{Shear Force} = V_t + \sqrt{\overline{V}^2_{3+4+\ldots+n_1} - \overline{V}^2_{1+2+\ldots+n_2}} \qquad \text{Eq. 4}$$

where $\overline{V}_{3+4}$ is the average reading of the MEMS3 and MEMS4 which read the total vector V. $\overline{V}_{1+2}$ is the average reading of the MEMS1 and MEMS2 which read only the normal component vector $V_n$. It is noted that for resolution in terms of space, the MEMS have to be 3 inches apart, illustrated at 504, in order for the external antenna to uniquely discern precisely which MEMS is reporting data. This tends to make the system approximate at this point in time. As further miniaturization is realized, this problem will be mitigated. Eventually the entire system will be on a single chip which can be used in very hard to reach places, including inside the human body.

Figure 6:
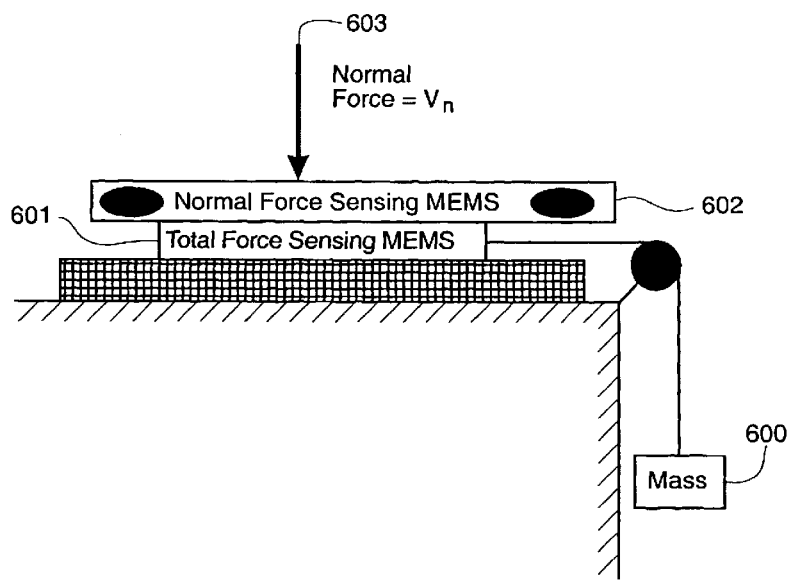
FIG. 6 shows a diagram of the invention illustrating shear force measurement.

To show the efficacy of the device described, herein, data were collected from the arrangement of FIG. 5 to sense total force, normal force, and the calculation of the resulting shear force. To show how the device can measure and distinguish total, normal, and shear stresses, a testing mechanism was constructed and is displayed in FIG. 6. In FIG. 6, the top, cantilever beam rectangle 602 contains the normal force sensing MEMS devices. The middle block 601 contains the MEMS which sense the total force vector including the normal force $V_n$, represented at 603 and a shear force induced by a mass over a pulley as shown at 600. The third block 604 below the total force sensing MEMS is used to provide friction so that no movement will occur. Also between the top two blocks, 601 and 602, the normal force $V_n$ at 603 was increased sufficiently so that the friction force between the top block 602 and the second block 601 was sufficiently large and had sufficient friction such that no movement would occur.

Figure 7:
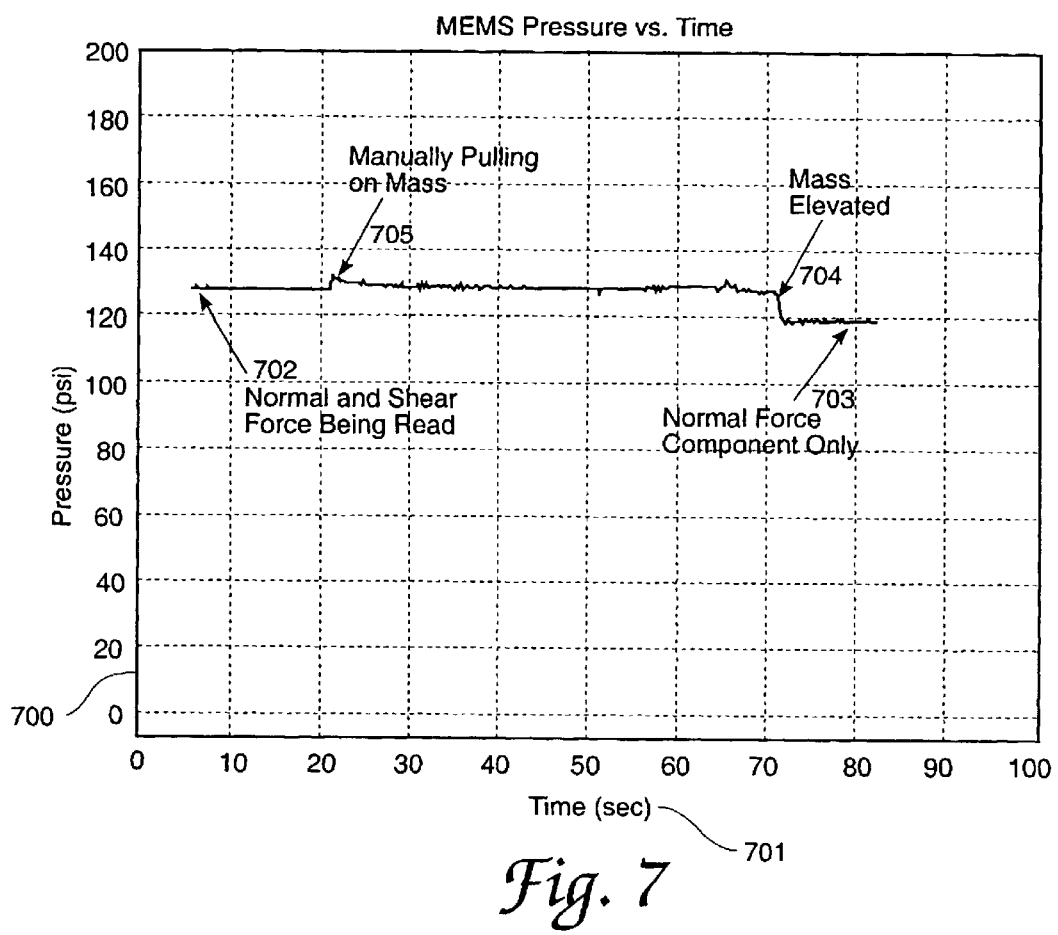
FIG. 7 shows a graph of data obtained from the arrangement of FIG. 6.

FIG. 7 illustrates the data obtained from the arrangement of the invention illustrated in FIGS. 5 and 6. FIG. 7 illustrates MEMs pressure versus time, the x-axis 701 representing time and the y-axis 700 representing pressure. After calibration and averaging, the left most side of the plot shows the pressure (force/unit area) reading 702 for the bottom MEMS sensors which measured both normal and shear forces. At about 22 seconds into the run, the mass was manually pulled downward slightly to show its effect on the bottom sensors, illustrated at 705. At approximately 72 seconds into the run, the mass being supported by the pulley was then lifted and consequently the bottom MEMS sensors read the same as the top sensors (the normal force $V_n$), illustrated at 704. It is emphasized that all MEMS sensors were calibrated with weights (normally) before the experiment was run. Since force is pressure times area, the individual MEMS are required to have their net pressure (normal) readings converted by a slightly different constant since the effective areas of their surfaces may differ slightly. To calibrate the shear force readings from FIG. 7, the following relationship would be used:

$$\text{Shear force} = (P_1 - P_2) * \text{effective area} \qquad \text{Eq. 5}$$

In FIG. 7, $P_1$ is the total force vector (pressure) of about 124.5 PSI and $P_2$ is the normal force vector (pressure) of about 118.5 PSI For this test, the Mass used was 10 pounds which means the effective area for the shear force calibration is:

$$\text{effective area} = \text{Shear Force}/(P_1 - P_2) = 10 \text{ pounds}/(124.5 - 118.5 \text{ PSI}) = 1.67 \text{ in}^2 \qquad \text{Eq. 6}$$

It is emphasized that the number 1.67 in$^2$ is only an effective area seen by the sensory system built in the Laboratory that particular day and may differ from the true physical dimensions of the MEMS sensors. This number is only for purposes of calibration and subsequent readings. This entire system described in FIG. 5 should be reduced down to a chip size to increase its accuracy and the calibrations should be performed at that level for a more miniaturized assemblage of FIG. 5.

In summary, the MEMS sensor thus described reads both normal and shear forces operable through nonmetallic materials, and is a passive device (it has no internal power source). The power for operation of the sensor is derived from the external antenna and thus it is completely wireless. The MEM sensor includes a novel cantilever beam configuration and algorithm, the readings of the MEMS sensors are averaged to reduce the experimental variability, to estimate the shear stress that may occur between a human and external equipment or possibly between materials. Finally, the shear force component is calculated via the formula:

$$\text{Shear Force} = V_f = \sqrt{\overline{V^2}_{3+4+\ldots+n_1} - \overline{V^2}_{1+2+\ldots+n_2}}$$

We claim:

1. A sensing apparatus responsive to shear forces applied thereto comprising:
   a first plurality of mechanical-electrical sensing components integral with a first rectangular structure and sensing normal forces;
   a second plurality of mechanical-electrical sensing components integral with a second rectangular structure adjacent and in a cantilever beam configuration to said first rectangular structure and sensing both normal and transverse forces;
   microelectronic processing means for reading force data obtained by said mechanical-electrical sensing components, temperature, and individual mechanical-electrical sensing component identifying data; and
   an operator interfacing external antenna transmitting power and an instructional signal to said mechanical-electrical sensing components and thereafter receiving said force, temperature and sensing component identifying data from said microelectronic processing means to determine shear force according to the relationship $$\text{Shear Force} = V_f = \sqrt{\overline{V^2}_{3+4+\ldots+n_1} - \overline{V^2}_{1+2+\ldots+n_2}}.$$

2. The sensing apparatus responsive to shear forces of claim 1 wherein said plurality of mechanical-electrical sensing components are at least 3 inches apart whereby said microelectronic processing means can uniquely discern precisely which mechanical-electrical sensing component is reporting data.

3. The sensing apparatus responsive to shear forces of claim 1 wherein an external radio frequency energy source powers said plurality of mechanical-electrical sensing components.

4. The sensing apparatus responsive to shear forces of claim 1 wherein said first and second plurality of mechanical-electrical sensing components are initially calibrated with normal forces.

5. The sensing apparatus responsive to shear forces of claim 1 wherein said first plurality of mechanical-electrical sensing components comprises two components, one on either end of said first rectangular structure.

6. The sensing apparatus responsive to shear forces of claim 1 wherein said second plurality of mechanical-electrical sensing components comprise two components.

7. The sensing apparatus responsive to shear forces of claim 1 wherein said first and second rectangular structures are rigid.

8. The sensing apparatus responsive to shear forces of claim 1 wherein said mechanical-electrical sensing components are piezoresistive sensors wherein resistivity is responsive to an applied force.

9. The sensing apparatus responsive to shear forces of claim 1 wherein said mechanical-electrical sensing components are piezoelectric sensors wherein magnetic properties are responsive to an applied force.

10. A wireless, robust sensing apparatus responsive to shear forces comprising:
    two mechanical-electrical normal force sensing components integral with and on opposing ends of a first, rigid rectangular structure;
    two mechanical-electrical sensing components integral with a second, rigid rectangular structure adjacent and in a cantilever beam configuration to said first rectangular structure and sensing both normal and transverse forces;
    said mechanical-electrical sensing components initially calibrated with normal forces;
    an external radio frequency energy source powering said mechanical-electrical sensing components;
    microelectronic processing means for reading force data obtained by said mechanical-electrical sensing components, temperature, and individual mechanical-electrical sensing component identifying data; and an operator interfacing external antenna transmitting a signal to said mechanical-electrical sensing components and thereafter receiving said force, temperature and sensing component identifying data from said microelectronic processing means to determine shear force according to the relationship $$\text{Shear Force} = V_t = \sqrt{\overline{V}^2_{3+4+\ldots+n_1} - \overline{V}^2_{1+2+\ldots+n_2}}.$$

11. The wireless, robust sensing apparatus responsive to shear forces of claim 10 wherein said mechanical-electrical sensing components are piezoelectric sensors.

12. The wireless, robust sensing apparatus responsive to shear forces of claim 10 wherein said mechanical-electrical sensing components are piezoresistive sensors.

13. A method for sensing shear forces comprising the steps of:

sensing normal forces using a first plurality of mechanical-electrical sensing components integral with a first rectangular structure;

configuring a second plurality of mechanical-electrical sensing components integral with a second rectangular structure adjacent and in a cantilever beam configuration to said first rectangular structure and;

sensing both normal and transverse forces using said mechanical-electrical sensing components from said configuring step;

reading force data obtained by said mechanical-electrical sensing components, and reading temperature, and individual mechanical-electrical sensing component identifying data using microelectronic processing means;

transmitting power and an instructional signal to said mechanical-electrical sensing components through an operator interfacing external antenna and thereafter receiving said force, temperature and sensing component identifying data from said microelectronic processing means and determining shear force according to the relationship $$\text{Shear Force} = V_t = \sqrt{\overline{V}^2_{3+4+\ldots+n_1} - \overline{V}^2_{1+2+\ldots+n_2}}.$$

14. The method of claim 13 for sensing shear forces wherein said sensing step further comprises the step of sensing normal forces using a first plurality of mechanical-electrical sensing components integral with and 3 inches apart on a first rectangular structure.

15. The method of claim 13 for sensing shear forces wherein said configuring step further comprises the step of configuring a second plurality of mechanical-electrical sensing components integral with and 3 inches apart on a second rectangular structure adjacent and in a cantilever beam configuration to said first rectangular structure.

16. The method of claim 13 for sensing shear forces further comprising, after said configuring step, the step of powering said mechanical-electrical sensing components by an external radio frequency energy source.

17. The method of claim 13 for sensing shear forces wherein said first and second plurality of mechanical-electrical sensing components from said sensing and configuring steps are piezoresistive sensors.

18. The method of claim 13 for sensing shear forces wherein said first and second plurality of mechanical-electrical sensing components from said sensing and configuring steps are piezoresistive sensors.

* * * * *

UNITED STATES PATENT AND TRADEMARK OFFICE
CERTIFICATE OF CORRECTION

PATENT NO.    : 6,736,015 B1
DATED         : May 18, 2004
INVENTOR(S)   : Daniel W. Repperger et al.

It is certified that error appears in the above-identified patent and that said Letters Patent is hereby corrected as shown below:

Column 1,
Line 41, no comma should appear after "$V_t$".
Line 43, no comma should appear after "$V_n$".

Column 3,
Line 3, "C+∈A/d" should read -- $C=\varepsilon A/d$ --.
Line 5, "∈" should read -- $\varepsilon$ --.

Column 5,
Line 30, a space should appear before "of".
Line 31, a period should follow "PSI".

Signed and Sealed this

Thirtieth Day of November, 2004

JON W. DUDAS
*Director of the United States Patent and Trademark Office*